US012582806B2

(12) United States Patent
El-Zawahry

(10) Patent No.: US 12,582,806 B2
(45) Date of Patent: Mar. 24, 2026

(54) FEMALE CATHETER GUIDE

(71) Applicant: The University of Toledo, Toledo, OH (US)

(72) Inventor: Ahmed El-Zawahry, Toledo, OH (US)

(73) Assignee: The University Of Toledo, Toledo, OH (US)

( * ) Notice: Subject to any disclaimer, the term of this patent is extended or adjusted under 35 U.S.C. 154(b) by 877 days.

(21) Appl. No.: 17/898,718

(22) Filed: Aug. 30, 2022

(65) Prior Publication Data

US 2023/0064729 A1     Mar. 2, 2023

Related U.S. Application Data

(60) Provisional application No. 63/238,547, filed on Aug. 30, 2021.

(51) Int. Cl.
| | |
|---|---|
| *A61M 25/00* | (2006.01) |
| *A61F 5/455* | (2006.01) |
| *A61M 25/06* | (2006.01) |

(52) U.S. Cl.
CPC ........... *A61M 25/06* (2013.01); *A61F 5/4553* (2013.01); *A61M 25/0017* (2013.01); *A61M 2202/0496* (2013.01); *A61M 2205/586* (2013.01); *A61M 2210/1475* (2013.01)

(58) Field of Classification Search
CPC .......... A61M 25/0017; A61M 25/0041; A61M 27/008; A61M 2210/1089; A61M 2210/1092
See application file for complete search history.

(56) References Cited

U.S. PATENT DOCUMENTS

| | | | | |
|---|---|---|---|---|
| 5,084,036 A | * | 1/1992 | Rosenbaum | .......... A61M 25/01 604/329 |
| 6,544,240 B1 | * | 4/2003 | Borodulin | ............. A61F 2/0009 604/329 |
| 7,104,980 B1 | * | 9/2006 | Laherty | ................. A61M 25/01 604/528 |
| 8,202,263 B2 | * | 6/2012 | Feloney | ................ A61F 5/4553 604/347 |
| 8,262,632 B2 | * | 9/2012 | Faber | ................ A61M 25/0017 604/528 |
| 11,642,492 B2 | * | 5/2023 | Murray | ................... A61F 5/455 604/544 |

\* cited by examiner

*Primary Examiner* — Catharine L Anderson
*Assistant Examiner* — Lynne Anderson
(74) *Attorney, Agent, or Firm* — MacMillan, Sobanski & Todd, LLC

(57)     ABSTRACT

A female urethral catheter guide includes a guide body defining a first body portion having a first end and a second body portion having a second end. The first body portion includes a longitudinally extending catheter support groove formed in a surface thereof, and the second body portion includes a radially outwardly extending tunnel portion having a catheter tunnel formed therein, wherein the catheter tunnel is connected to the catheter support groove and the second end of the second body portion is rounded and defines a vaginal support end.

12 Claims, 5 Drawing Sheets

FEMALE CATHETER GUIDE

BACKGROUND OF THE INVENTION

This invention relates in general to female urethral catheters. In particular, this invention relates to a female urethral catheter guide with an improved structure that simplifies the ability of a user to insert a catheter into the female urethra, and is designed to be simple, easy to use, and affordable.

Catheters are used for many different urinary and medical conditions. Self-catheterization in commonly used for patients with urinary abnormalities. Catheters are also commonly used in patients who have problems with urinary retention or other voiding dysfunction issues. Female urethral catheterization is an often difficult procedure and requires good use of both hands, good knowledge of anatomy, and good handling and manipulation of the catheter. One major problem is that women are not able to see the location of their urethra to be able to insert the catheter correctly. Improper catheterization may result in the waste of catheters, catheter contamination, and possible patient infection. In addition, patient fear from catheterization may dissuade many from compliance. For example, if the catheter is inadvertently introduced into the vagina prior to being introduced into the urethra, the catheter may become contaminated with vaginal flora which will carry a higher risk of urinary tract infection.

The difficulty of the procedure may be more pronounced in patients with a larger body mass index (BMI) and in patients with postural problems. Self-catheterization is the preferred option for treatment when patients cannot void volitionally. The alternative is placing a permanent catheter. Permanent catheters are associated with much higher risk of complications, including recurrent urinary tract infection, urinary calculi, patient pain and discomfort and very significant urethral and bladder erosion. These conditions will require significant additional costs to treat. Thus, self-catheterization is a better option, however and unfortunately, with the difficulty in reaching the female urethra, a solution is needed to mitigate the challenges in patients with these conditions. On major concern is that self-catheterization is not always easy to teach and may not be easy to adopt by many patients. Self-catheterization may be hampered by the difficulty to localize the urethra, an inability to visualize the anatomy, poor dexterity, or poor accessibility to the urethra.

Thus, it would be desirable to provide an improved device for a female urethral catheter as a guide that allows health care workers to place female catheters more easily and with less manipulation, helps female patients to more easily place their catheters during self-catheterization, helps reduce the chances of trauma to the urethral opening, and maintains a clean and sterile environment during female catheter insertion, thus reducing the risk of infection.

SUMMARY OF THE INVENTION

This invention relates to a female urethral catheter guide with an improved structure that simplifies the ability of a user to insert a catheter into the urethra, and is designed to be simple, ergonomic, easy to use, and affordable. It also will provide means to minimize contact with the patient's skin or vaginal flora during insertion.

In use, the female urethral catheter guide enhances the ability of either health care workers or the patient to place the catheter in female patients with a no-touch technique that will help to reduce risks of contamination and infection. Women who may have been concerned with the difficulty of self-catheterization will be able to self-insert a catheter easily and with less manipulation than is required with known self-catheterization devices and techniques. The female urethral catheter guide will encourage patients' compliance, improve care and eventually decrease cost to both the patients and healthcare system.

One embodiment of the female urethral catheter guide includes a guide body defining a first body portion having a first end and a second body portion having a second end. The first body portion, which the patient will be holding, includes a longitudinally extending catheter support groove formed in a surface thereof (this will help the patient to guide the catheter under vision), and the second body portion includes a radially outwardly extending tunnel portion having a catheter tunnel formed therein, wherein the catheter tunnel is connected to the catheter support groove and the second end of the second body portion is rounded and defines a vaginal support end. This second portion will host the catheter as it is guided to the urethra. This will minimize catheter contract to the skin and vagina, and will lessen the chance of the catheter to miss the target, i.e., the urethral opening.

In another embodiment, the female urethral catheter guide includes a guide body having a first end and a second end, and a longitudinally extending catheter support groove formed in a surface of the guide body, wherein the second end of the guide body is rounded and defines a vaginal support end.

In an additional embodiment, the female urethral catheter guide includes a guide body having a flat first surface, a rounded second surface, and rounded side edges between the first surface and the second surface. The guide body has a proximal end and a distal end, wherein the distal end is rounded and defines a vaginal support end. A tunnel portion extends outwardly from the second surface aft of the vaginal support end and has a catheter tunnel formed therein. The catheter tunnel is generally cylindrical, and a distal portion thereof extends at an acute angle from a longitudinally extending center line of the guide body. A longitudinally extending catheter support groove is formed in the second surface from the proximal end to a proximal end of the catheter tunnel.

In a further embodiment, the female urethral catheter guide includes a guide body having a flat first surface, a rounded second surface, and rounded side edges between the first surface and the second surface, wherein the guide body has a proximal end and a distal end, and wherein the distal end is rounded and defines a vaginal support end. A longitudinally extending first portion of a catheter support groove is formed in a surface of the guide body, and a catheter portion extends radially outwardly from the distal end the guide body portion and has a second portion of the catheter support groove formed therein.

Various aspects of this invention will become apparent to those skilled in the art from the following detailed description of the preferred embodiment, when read in light of the accompanying drawings.

DETAILED DESCRIPTION OF THE PREFERRED EMBODIMENT

Figures 1, 2, 3:
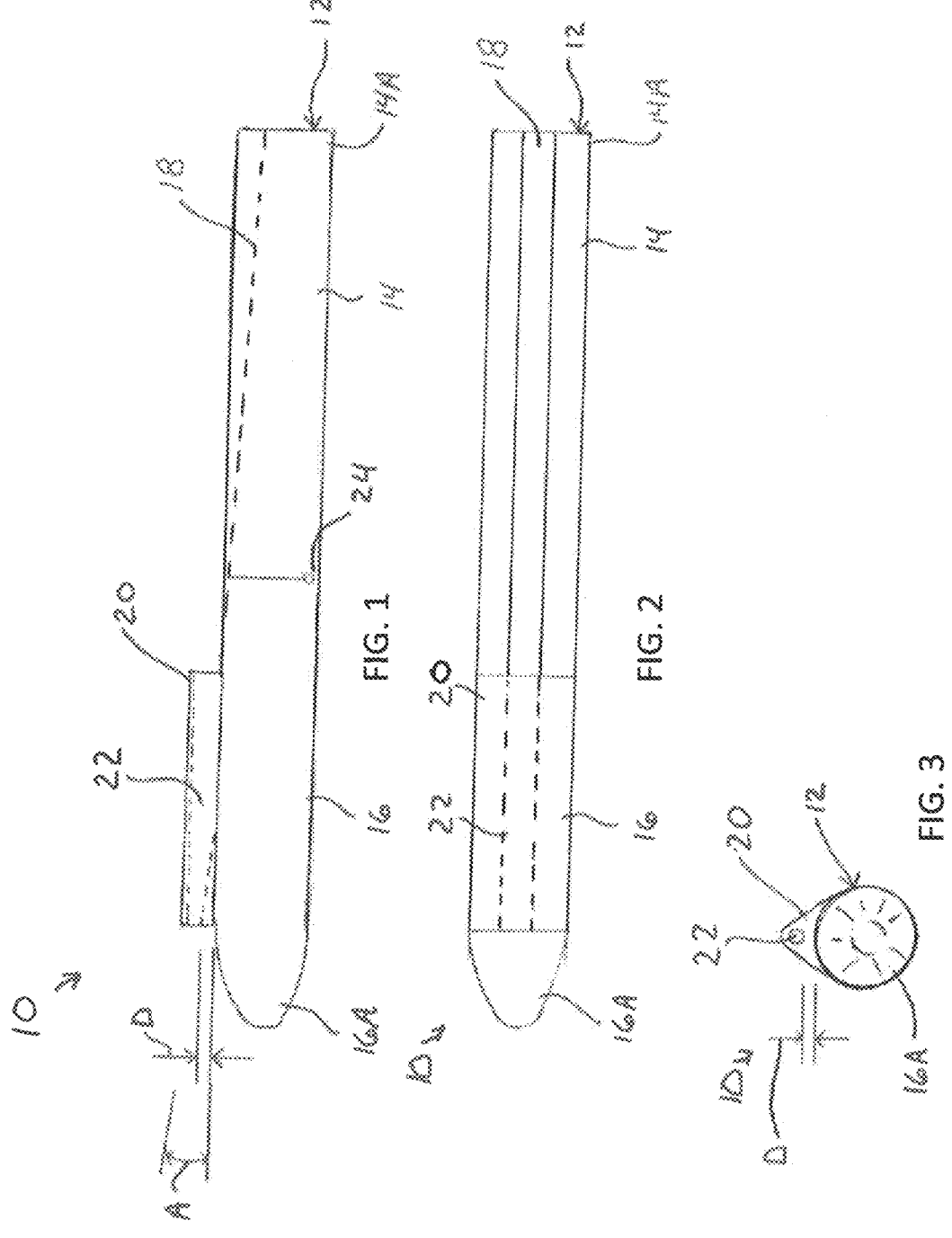
FIG. 1 is an elevational view of the first embodiment of the female urethral catheter guide according to this invention.
FIG. 2 is a top plan view of the first embodiment of the female urethral catheter guide illustrated in FIG. 1.
FIG. 3 is an end view of the first embodiment of the female urethral catheter guide illustrated in FIGS. 1 and 2.

Referring now to the drawings, there is illustrated at 10 in FIGS. 1 through 3 a first embodiment of a female urethral catheter guide according to this invention. The female urethral catheter guide 10 includes a guide body 12. The guide body 12 includes a generally cylindrical first body portion 14 having a first or proximal end 14A and a second body portion 16 having a second or distal end 16A. The distal end is rounded and defines a vaginal support end 16A.

A longitudinally extending catheter support groove 18 is formed in a surface of the first body portion 14 (the upwardly facing surface when viewing FIG. 1). In the illustrated embodiment, the catheter support groove 18 has a diameter of about 5.5 mm. Alternatively, the catheter support groove 18 may have a diameter with the range of about 5.5 mm to about 7 mm. Additionally, the catheter support groove 18 has a first depth at the proximal end 14A and a second depth at a distal end of the first body portion 14, wherein the first depth is larger than the second depth.

In the illustrated embodiment, the guide body 12 is generally cylindrical or oval in shape to be ergonomic, has a diameter of about 2.5 cm, and length of about 15 cm. Alternatively, the guide body 12 may have any other desired shape, such as having an oval cross-section, of having any other desired shape to improve its ergonomic design. The guide body 12 may have a diameter within the range of about 2 cm to about 3 cm and a length within the range of about 10 cm to about 20 cm.

The second body portion 16 includes a radially outwardly extending tunnel portion 20 (the upwardly facing portion when viewing FIG. 1) having a catheter tunnel 22 formed therein. The illustrated catheter tunnel 22 is enclosed, however, the catheter tunnel 22 may have an open roof or upper portion if desired. The catheter tunnel 22 is generally cylindrical and a distal end thereof extends at an acute angle A from a longitudinally extending center line of the guide body 12. In the illustrated embodiment, the angle A is about 15 degrees. Alternatively, the angle A may be any desired angle, such as an angle within the range of about 15 degrees to about 30 degrees. The illustrated tunnel 22 has a diameter of about 7 mm. Alternatively, the tunnel 22 may have a diameter with the range of about 5.5 mm to about 7.5 mm. In most patients, the urethra is within the range of about 1.0 mm to about 2.0 mm above the vaginal opening. Thus, a distal end of the illustrated tunnel 22 is also spaced apart from the surface of the vaginal support end 16A (the upwardly facing surface when viewing FIG. 1) by a distance D of about 1.0 mm to about 2.0 mm.

If desired, the guide body 12 may be foldable and thus may include a joint, such as a hinged joint shown schematically at 24 in FIG. 1. Thus, the female urethral catheter guide 10 having such a hinged joint 24 may be folded so that it may be more easily carried, such as in a bag or in a pocket.

The female urethral catheter guide 10 may be formed from any desired material, including but not limited to polyurethane, rubber, copper, aluminum, and other plastics, metal, non-metal, composites, and combinations thereof. It will be understood that the choice of material may be determined through routine experimentation and may be dictated by cost. The female urethral catheter guide 10 may be manufactured to be disposable or reusable.

Figures 4, 5, 6:
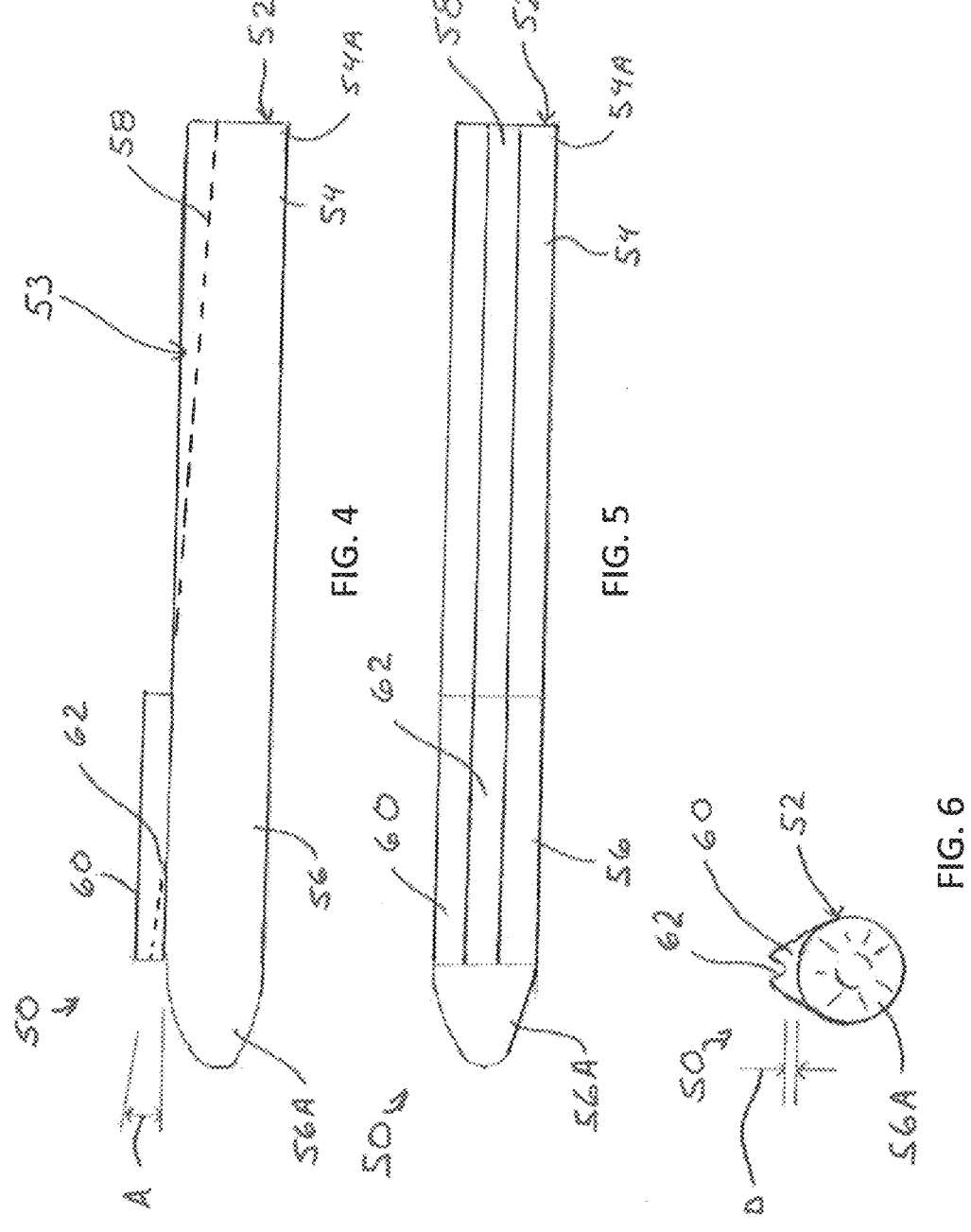
FIG. 4 is an elevational view of the second embodiment of the female urethral catheter guide according to this invention.
FIG. 5 is a top plan view of the second embodiment of the female urethral catheter guide illustrated in FIG. 4.
FIG. 6 is an end view of the second embodiment of the female urethral catheter guide illustrated in FIGS. 4 and 5.
Figures 7, 7A, 7B, 7C:
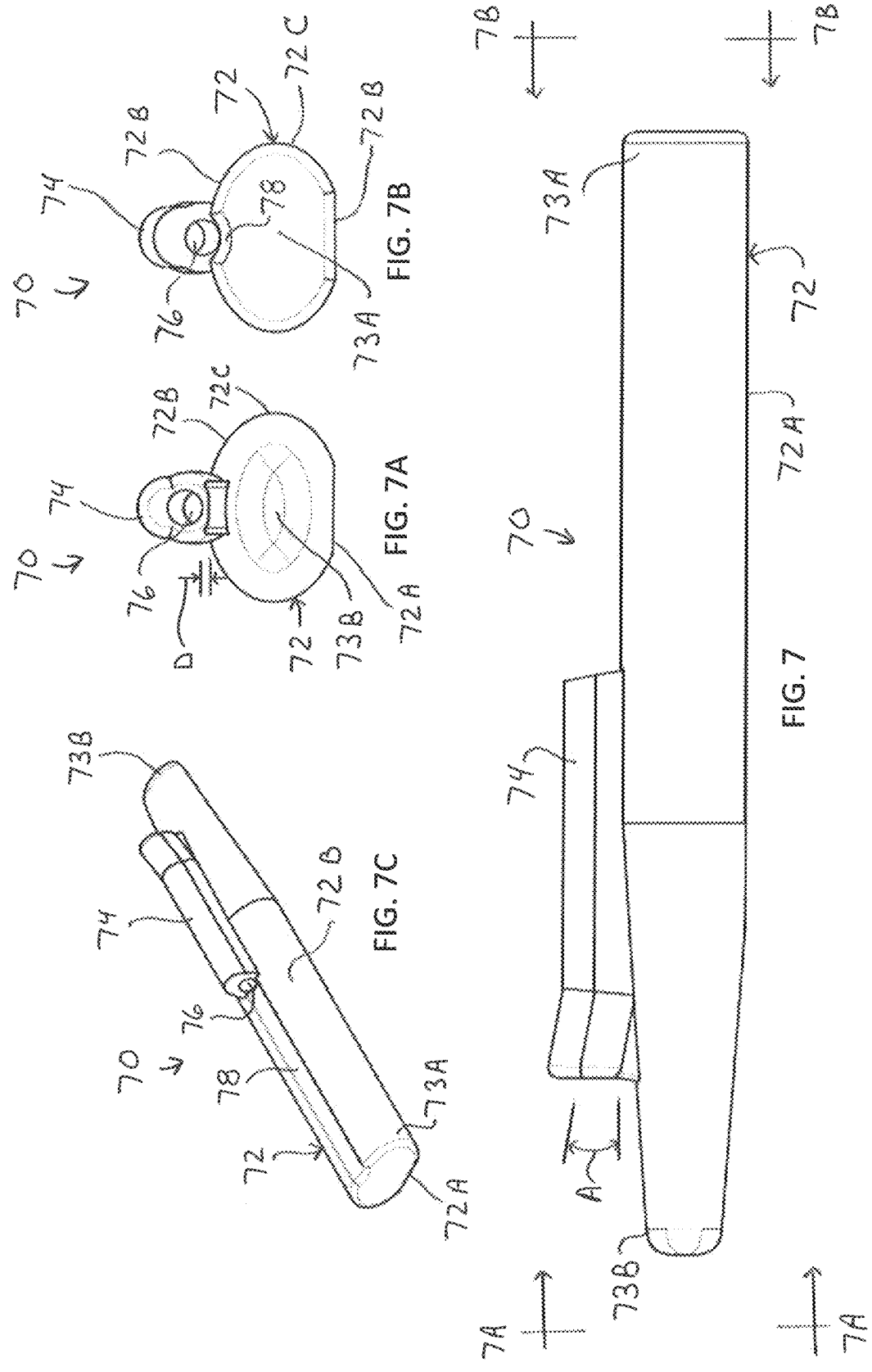
FIG. 7 is an elevational view of the third embodiment of the female urethral catheter guide according to this invention.
FIG. 7A is a first end view of the third embodiment of the female urethral catheter guide illustrated in FIG. 7.
FIG. 7B is a second end view of the third embodiment of the female urethral catheter guide illustrated in FIG. 7.
FIG. 7C is a perspective view of the third embodiment of the female urethral catheter guide illustrated in FIG. 7.
Figures 8, 8A, 8B, 8C:
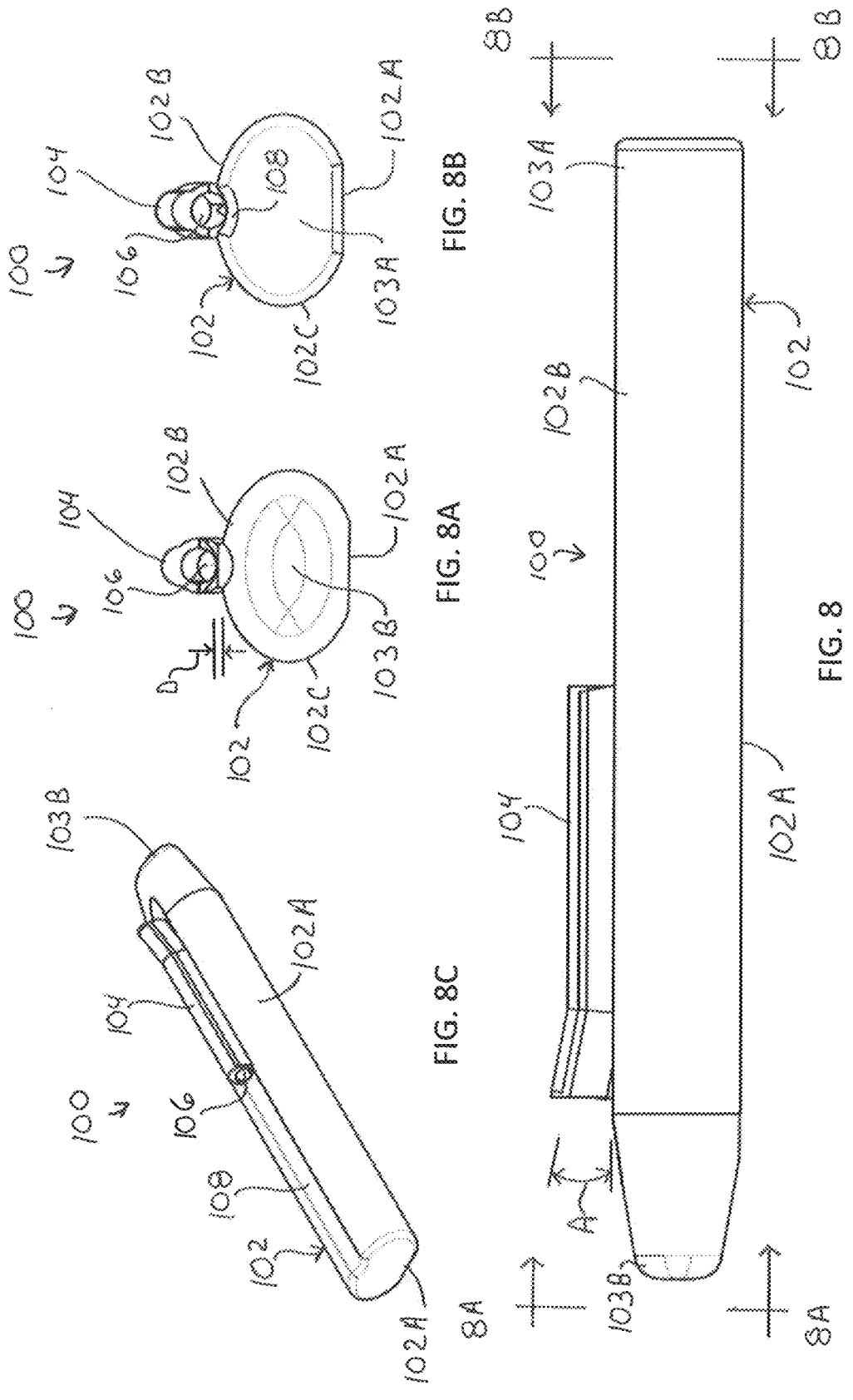
FIG. 8 is an elevational view of the fourth embodiment of the female urethral catheter guide according to this invention.
FIG. 8A is a first end view of the fourth embodiment of the female urethral catheter guide illustrated in FIG. 8.
FIG. 8B is a second end view of the fourth embodiment of the female urethral catheter guide illustrated in FIG. 8.
FIG. 8C is a perspective view of the fourth embodiment of the female urethral catheter guide illustrated in FIG. 8.
Figures 9, 9A, 9B, 9C:
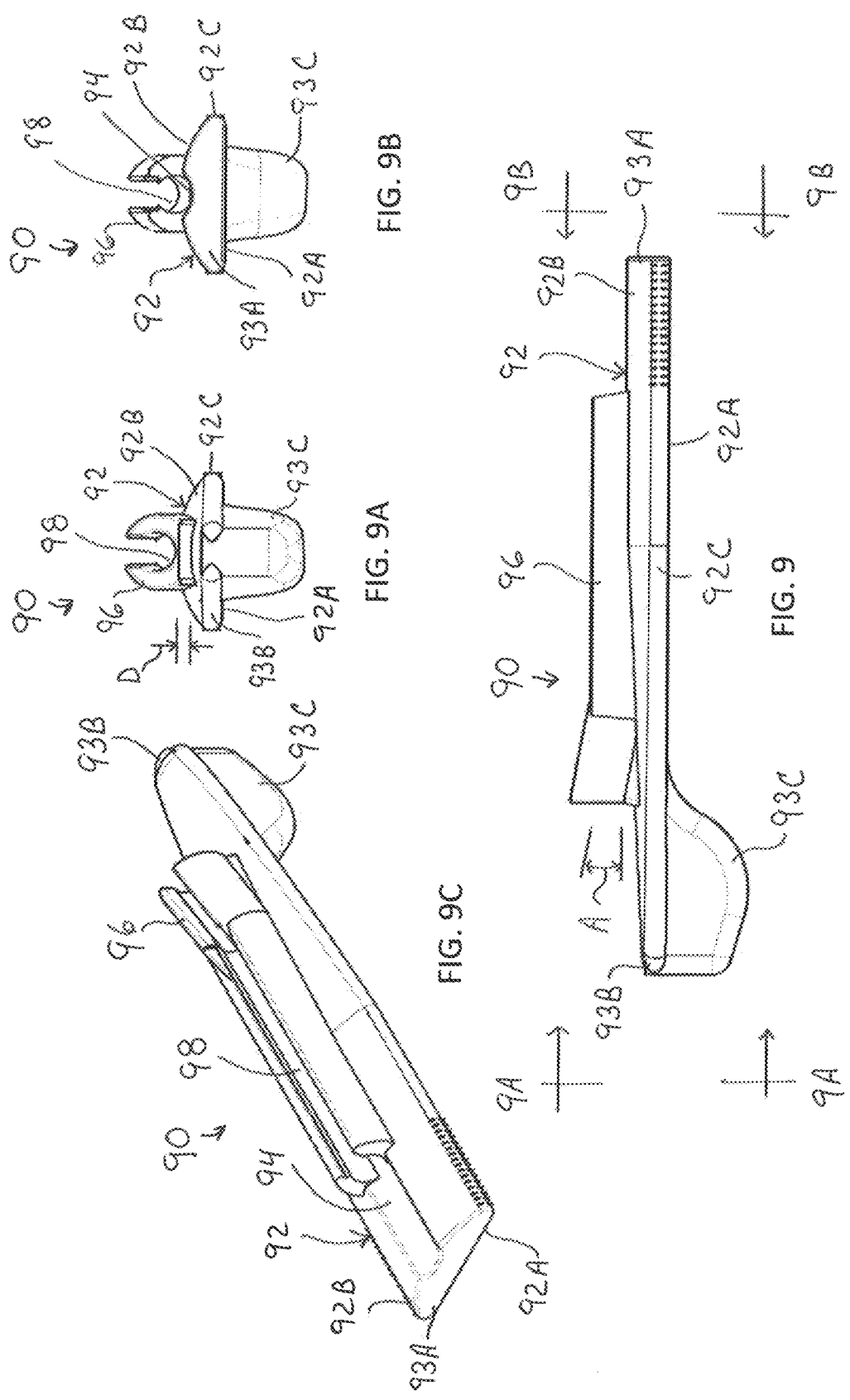
FIG. 9 is an elevational view of the fifth embodiment of the female urethral catheter guide according to this invention.
FIG. 9A is a first end view of the fifth embodiment of the female urethral catheter guide illustrated in FIG. 9.
FIG. 9B is a second end view of the fifth embodiment of the female urethral catheter guide illustrated in FIG. 9.
FIG. 9C is a perspective view of the fifth embodiment of the female urethral catheter guide illustrated in FIG. 9.

Referring now to FIGS. 4 through 6, a second embodiment of the female urethral catheter guide is shown generally at 50. The female urethral catheter guide 50 is similar to the female urethral catheter guide 10 and includes a guide body 52. The guide body 52 includes a generally cylindrical first body portion 54 having a first or proximal end 54A and a second body portion 56 having a second or distal end. The distal end is rounded and defines a vaginal support end 56A.

The female urethral catheter guide 50 includes a longitudinally extending catheter support groove 53 formed in a surface of the guide body 52. In the illustrated embodiment, the longitudinally extending catheter support groove 53 includes a longitudinally extending first catheter support groove 58 formed in a surface of the first body portion 54 (the upwardly facing surface when viewing FIG. 4) and a second catheter support groove 62, described below. The illustrated first catheter support groove 58 has a first depth at the proximal end 54A and a second depth at a distal end of the first body portion 54, wherein the first depth is larger than the second depth.

The second body portion 56 includes a radially outwardly extending catheter portion 60 (the upwardly facing portion when viewing FIG. 4) having the second catheter support groove 62 formed therein. The second catheter support groove 62 has a semi-cylindrical inside surface and a distal end thereof extends at the angle A from a longitudinally extending center line of the guide body 52. In the illustrated embodiment, the angle A is about 15 degrees. Alternatively, the angle A may be any desired angle, such as an angle within the range of about 15 degrees to about 30 degrees.

The illustrated first and second catheter support grooves 58 and 62 have a diameter of about 7 mm. Alternatively, the first and second catheter support grooves 58 and 62 may have a diameter with the range of about 5.5 mm to about 7.5 mm. Like the tunnel 22 of the female urethral catheter guide 10, a distal end of the illustrated second catheter support groove 62 is also spaced apart from the surface of the vaginal support end 56A (the upwardly facing surface when viewing FIG. 4) by a distance D of about 1.0 mm to about 2.0 mm.

In use, the female urethral catheter guide 10 may be positioned on the patient such that the vaginal support end 16A is inserted in the patient's vagina. In this position, the distal end of the catheter tunnel 22 is positioned near the urethral opening. In most patients, the urethra is within the range of about 1.0 mm to about 2.0 mm above the vaginal opening. When urged toward the patient, a catheter mounted in the female urethral catheter guide 10 will slide forwardly (toward the patient) at the angle A, and thus toward and into the urethral opening.

Once the catheter is inserted in the patient, the female urethral catheter guide 10 will remain in place relative to the catheter and to the patient while the patient empties her bladder. After urination, the catheter may be removed by simultaneously moving the female urethral catheter guide 10, and the catheter mounted thereon, away from the patient, thus making it unnecessary to remove the catheter from the catheter tunnel 22 of the female urethral catheter guide 10.

Advantageously, the vaginal support end 16A of the guide body 12, when inserted into the vagina, creates a secure and stable base for the user. The catheter tunnel portion 20 and its angled catheter tunnel 22 allows the catheter to be directed into the urethra. The user is required to only touch a proximal portion of the catheter using the sterile outer packaging of the catheter while guiding the catheter into the urethra with the female urethral catheter guide 10, thus allowing for catheter insertion without the user touching the catheter. This ability to insert the catheter without the user touching the catheter and the prevention of inadvertent catheter insertion into the vagina prior to insertion into the urethra also significantly reduces the risk of contamination and possible infections from such contamination. Patients who may have been reluctant to attempt self-catheterization with known insertion devices and guides, will be able to perform self-catheterization more easily and with less manipulation than with known insertion devices and guides.

The design of the female urethral catheter guide 50 may make it more advantageous for use in a hospital or institutional setting. In such hospital or institutional settings, as catheters may remain in the patient for longer periods of time. Additionally, because a proximal end of the catheter would be connected to a collection bag, there would be no way to remove the female urethral catheter guide if it included the catheter tunnel 22 of the female urethral catheter guide 10.

A third embodiment of the female urethral catheter guide is shown generally at 70 in FIGS. 7 and 7A, 7B, and 7C. The female urethral catheter guide 70 is similar to the female urethral catheter guide 10 and includes a guide body 72. The guide body 72 includes a generally flat first or bottom surface 72A, a generally rounded second or top surface 72B and rounded side edges 72C between the bottom surface 72A and the top surface 72B. The guide body 72 has a first or proximal end 73A and a second or distal end. The distal end is rounded and defines a vaginal support end 73B.

A tunnel portion 74 extends radially from the top surface 72B aft of the vaginal support end 73B and has a catheter tunnel 76 formed therein. The catheter tunnel 76 is generally cylindrical and a distal end thereof extends at the angle A from a longitudinally extending center line of the guide body 72. As described above, the angle A is about 15 degrees. The illustrated catheter tunnel 76 has a diameter of about 7 mm.

A longitudinally extending catheter support groove 78 is formed in the top surface 72B. In the illustrated embodiment, the catheter support groove 78 has a diameter of about 5.5 mm. Alternatively, the catheter support groove 78 may have a diameter with the range of about 5.5 mm to about 7.5 mm. Additionally, the catheter support groove 78 may have a first depth at the proximal end 73A and a second depth at a distal end thereof, i.e., where the catheter support groove 78 meets the catheter tunnel 76, wherein the first depth is larger than the second depth.

In the illustrated embodiment, the guide body 72 has length of about 15 cm and a width of about 3 cm. Alternatively, the guide body 72 may have any other desired length and width, such as a length within the range of about 12 cm to about 25 cm and a width within the range of about 2 cm to about 3.5 cm. A distal opening of the catheter tunnel 76 is spaced apart from the vaginal support end 73B by the distance D.

A fourth embodiment of the female urethral catheter guide is shown generally at 100 in FIGS. 8 and 8A, 8B, and 8C. The female urethral catheter guide 100 is similar to the female urethral catheter guide 70 and includes a guide body 102. The guide body 102 includes a generally flat first or bottom surface 102A, a generally rounded second or top surface 102B and rounded side edges 102C between the bottom surface 102A and the top surface 102B. The guide body 102 has a first or proximal end 103A and a second or distal end. The distal end is rounded and defines a vaginal support end 103B.

A tunnel portion 104 extends radially from the top surface 102B aft of the vaginal support end 103B and has a catheter tunnel 106 formed therein. The catheter tunnel 106 is generally cylindrical and a distal end thereof extends at the angle A from a longitudinally extending center line of the guide body 102. As described above, the angle A is about 15 degrees. The illustrated catheter tunnel 106 has a diameter of about 7 mm.

A longitudinally extending catheter support groove 108 is formed in the top surface 102B. In the illustrated embodiment, the catheter support groove 108 has a diameter of about 5.5 mm. Alternatively, the catheter support groove 108 may have a diameter with the range of about 5.5 mm to about 7.5 mm. Additionally, the catheter support groove 108 may have a first depth at the proximal end 103A and a second depth at a distal end thereof, i.e., where the catheter support groove 108 meets the catheter tunnel 106, wherein the first depth is larger than the second depth.

In the illustrated embodiment, the guide body 102 has length of about 15 cm and a width of about 3 cm. Alternatively, the guide body 102 may have any other desired length and width, such as a length within the range of about 12 cm to about 25 cm and a width within the range of about 2 cm to about 3.5 cm. A distal opening of the catheter tunnel 106 is spaced apart from the vaginal support end 103B by the distance D.

A fifth embodiment of the female urethral catheter guide is shown generally at 90 in FIGS. 9, and 9A, 9B, and 9C. The female urethral catheter guide 90 is similar to the female urethral catheter guide 50 and includes a guide body 92. The guide body 92 includes a generally flat first or bottom surface 92A, a generally rounded second or top surface 92B and rounded side edges 92C between the bottom surface 92A and the top surface 92B. The guide body 92 has a first or proximal end 93A and a second or distal end. The distal end is rounded and defines a vaginal support end 93B. The illustrated vaginal support end 93B a bottom portion 93C that extends outwardly from the vaginal support end 93B

(downwardly when viewing FIG. 9) and extends outwardly beyond the bottom surface 92A of the guide body 92.

Like the female urethral catheter guide 50, the guide body 92 includes a longitudinally extending first catheter support groove 94 formed in the top surface 92B. The guide body 92 also includes a catheter portion 96 that extends radially outwardly from the top surface 92B aft of the vaginal support end 93B and has a second catheter support groove 98 formed therein. The second catheter support groove 98 has a semi-cylindrical inside surface and a distal portion thereof extends at the angle A from a longitudinally extending center line of the guide body 92. In the illustrated embodiment, the angle A is about 15 degrees. Alternatively, the angle A may be any desired angle, such as an angle within the range of about 15 degrees to about 30 degrees.

The illustrated first and second catheter support grooves 94 and 98 have a diameter of about 7 mm. Alternatively, the first and second catheter support grooves 94 and 98 may have a diameter with the range of about 5.5 mm to about 7 mm. Like the tunnel 22 of the female urethral catheter guide 10, a distal end of the illustrated second catheter support groove 98 is also spaced apart from vaginal support end 93B (the upwardly facing surface when viewing FIG. 9) by the distance D of about 1.0 mm to about 2.0 mm.

The principle and mode of operation of this invention have been explained and illustrated in its preferred embodiment. However, it must be understood that this invention may be practiced otherwise than as specifically explained and illustrated without departing from its spirit or scope.

What is claimed is:

1. A female urethral catheter guide comprising:
a guide body defining a first body portion having a first end and a second body portion having a second end;
wherein the first body portion is generally cylindrical and includes a longitudinally extending catheter support groove formed in a surface thereof; and
wherein the second body portion includes a radially outwardly extending tunnel portion having a catheter tunnel formed therein, the catheter tunnel connected to the catheter support groove;
wherein the second end of the second body portion is rounded and defines a vaginal support end; and
wherein the longitudinally extending catheter support groove has a first depth at a proximal end of the guide body and a second depth at a distal end of the first body portion, wherein the first depth is larger than the second depth.

2. The female urethral catheter guide according to claim 1, wherein the first body portion defines a handle.

3. The female urethral catheter guide according to claim 1, wherein the catheter tunnel is generally cylindrical, and wherein a distal portion thereof extends at an acute angle from a longitudinally extending center line of the guide body.

4. The female urethral catheter guide according to claim 1, wherein a distal opening of the catheter tunnel is spaced apart from a surface of the vaginal support end by a distance of about 1.0 mm to about 2.0 mm.

5. The female urethral catheter guide according to claim 1, wherein the guide body includes a hinge and is foldable.

6. A female urethral catheter guide comprising:
a guide body having a first end and a second end; and
a longitudinally extending catheter support groove formed in a surface of the guide body;
wherein the second end of the guide body is rounded and defines a vaginal support end;

wherein the guide body further includes a first body portion having a first end and a second body portion having a second end;
wherein the catheter support groove includes a longitudinally extending first catheter support groove formed in a surface of the first body portion; and
wherein the first catheter support groove has a first depth at a proximal end of the first body portion and a second depth at a distal end of the first body portion, wherein the first depth is larger than the second depth.

7. The female urethral catheter guide according to claim 6, wherein the second body portion includes a radially outwardly extending catheter portion having a second catheter support groove formed therein.

8. The female urethral catheter guide according to claim 7, wherein the second catheter support groove has a semi-cylindrical inside surface, and wherein a distal portion thereof extends at an acute angle from a longitudinally extending center line of the guide body.

9. The female urethral catheter guide according to claim 8, wherein a distal end of the second catheter support groove is spaced apart from a surface of the vaginal support end by a distance of about 1.0 mm to about 2.0 mm.

10. A female urethral catheter guide comprising:
a guide body having a flat first surface, a rounded second surface, and rounded side edges between the first surface and the second surface;
wherein the guide body has a proximal end and a distal end, wherein the distal end is rounded and defines a vaginal support end; and
a tunnel portion extending outwardly from the second surface aft of the vaginal support end and having a catheter tunnel formed therein;
wherein the catheter tunnel is generally cylindrical, and wherein a distal portion thereof extends at an acute angle from a longitudinally extending center line of the guide body;
wherein a longitudinally extending catheter support groove is formed in the second surface from the proximal end to a proximal end of the catheter tunnel; and
wherein the longitudinally extending catheter support groove has a first depth at a proximal end of the guide body and a second depth at a distal end thereof, and wherein the first depth is larger than the second depth.

11. The female urethral catheter guide according to claim 10, wherein a distal opening of the catheter tunnel is spaced apart from a surface of the vaginal support end by a distance of about 1.0 mm to about 2.0 mm.

12. A female urethral catheter guide comprising:
a guide body having a flat first surface, a rounded second surface, and rounded side edges between the first surface and the second surface, wherein the guide body has a proximal end and a distal end, and wherein the distal end is rounded and defines a vaginal support end;
a longitudinally extending first portion of a catheter support groove formed in a surface of the guide body; and
a catheter portion extending radially outwardly from the distal end the guide body portion and having a second portion of the catheter support groove formed therein;
wherein the second portion of the catheter support groove has a semi-cylindrical inside surface, and wherein a distal portion thereof extends at an acute angle from a longitudinally extending center line of the guide body; and wherein a distal end of the second portion of the catheter support groove is spaced apart from a surface of the vaginal support end by a distance of about 1.0 mm to about 2.0 mm.

\* \* \* \* \*